(12) United States Patent
Buccieri et al.

(10) Patent No.: US 11,406,548 B2
(45) Date of Patent: Aug. 9, 2022

(54) OBSTACLE DETECTION IR BEAM FILTER

(71) Applicant: Hill-Rom Services, Inc., Batesville, IN (US)

(72) Inventors: Michael Buccieri, Greenfield, IN (US); James L. Walke, Batesville, IN (US); Chris L. Hildenbrand, Greensburg, IN (US); John G. Byers, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 214 days.

(21) Appl. No.: 16/559,731

(22) Filed: Sep. 4, 2019

(65) Prior Publication Data

US 2020/0100964 A1    Apr. 2, 2020

Related U.S. Application Data

(60) Provisional application No. 62/737,504, filed on Sep. 27, 2018.

(51) Int. Cl.
| | | |
|---|---|---|
| *A61G 7/05* | (2006.01) | |
| *A61G 7/008* | (2006.01) | |
| *A61G 7/018* | (2006.01) | |
| *A61B 6/04* | (2006.01) | |
| *A61G 7/10* | (2006.01) | |

(52) U.S. Cl.
CPC ............ *A61G 7/0524* (2016.11); *A61G 7/008* (2013.01); *A61G 7/018* (2013.01); *A61B 6/0407* (2013.01); *A61G 7/1038* (2013.01)

(58) Field of Classification Search
CPC ...... A61G 7/0524; A61G 7/008; A61G 7/018; A61G 7/1038; A61G 2203/726; A61B 6/0407
See application file for complete search history.

(56) References Cited

U.S. PATENT DOCUMENTS

| | | | |
|---|---|---|---|
| 1,078,077 | A | 11/1913 | Arnold |
| 2,527,111 | A | 10/1950 | Widrich |
| 2,900,521 | A | 8/1959 | Eames |
| 3,704,396 | A | 11/1972 | Macdonald |
| 3,742,222 | A | 6/1973 | Endl |
| 3,746,863 | A | 7/1973 | Pronovost |
| 3,805,061 | A | 4/1974 | De Missimy et al. |

(Continued)

FOREIGN PATENT DOCUMENTS

| | | |
|---|---|---|
| CN | 1211307 | 3/1999 |
| CN | 1420753 A | 5/2003 |

(Continued)

OTHER PUBLICATIONS

Chinese counterpart application Office Action dated Feb. 3, 2021 and translation (10 pages).

(Continued)

*Primary Examiner* — Eric J Kurilla
(74) *Attorney, Agent, or Firm* — Barnes & Thornburg LLP (57) ABSTRACT

A patient-support apparatus includes a first frame and a second frame movable relative to the first frame. The patient-support apparatus further includes an obstacle detection device and related method for detecting an obstacle between the first frame and the second frame of the patient-support apparatus.

18 Claims, 7 Drawing Sheets

(56) References Cited

U.S. PATENT DOCUMENTS

| | | | |
|---|---|---|---|
| 3,858,043 A | 12/1974 | Sick et al. | |
| 3,875,403 A | 4/1975 | Svensson | |
| 3,970,846 A | 7/1976 | Schofield, Jr. et al. | |
| 4,023,887 A | 5/1977 | Speers | |
| 4,266,124 A | 5/1981 | Weber et al. | |
| 4,325,061 A | 4/1982 | Wolar | |
| 4,385,508 A | 5/1983 | Schimko | |
| 4,403,214 A | 9/1983 | Wolar | |
| 4,463,463 A | 8/1984 | Kaneko | |
| 4,520,262 A | 5/1985 | Denton | |
| 4,534,077 A | 8/1985 | Martin | |
| 4,552,403 A | 11/1985 | Yindra | |
| 4,645,920 A | 2/1987 | Carroll et al. | |
| 4,724,554 A | 2/1988 | Kowalski et al. | |
| 4,794,248 A | 12/1988 | Gray | |
| 4,837,877 A | 6/1989 | Hamada et al. | |
| 4,882,566 A * | 11/1989 | Koerber, Sr. | A61G 7/018 |
| | | | 340/12.22 |
| 4,921,295 A | 5/1990 | Stollenwerk | |
| 4,960,271 A | 10/1990 | Sebring | |
| 5,020,169 A | 6/1991 | Hamada et al. | |
| RE33,668 E | 8/1991 | Gray | |
| 5,156,166 A | 10/1992 | Sebring | |
| 5,181,288 A | 1/1993 | Heaton et al. | |
| 5,280,622 A | 1/1994 | Tino | |
| 5,317,769 A | 6/1994 | Weismiller et al. | |
| 5,468,216 A | 11/1995 | Johnson et al. | |
| 5,495,228 A | 2/1996 | Futsuhara et al. | |
| 5,567,931 A | 10/1996 | Amend et al. | |
| 5,696,362 A | 12/1997 | Amend | |
| 5,758,371 A | 6/1998 | VanDyke et al. | |
| 5,984,404 A | 11/1999 | Novoa et al. | |
| 6,161,891 A | 12/2000 | Blakesley | |
| 6,167,991 B1 | 1/2001 | Full et al. | |
| 6,199,508 B1 | 3/2001 | Miale et al. | |
| 6,208,250 B1 | 3/2001 | Dixon et al. | |
| 6,320,510 B2 | 11/2001 | Menkedick et al. | |
| 6,351,861 B1 | 3/2002 | Shows et al. | |
| 6,354,716 B1 | 3/2002 | Chen et al. | |
| 6,662,391 B2 | 12/2003 | Wilson et al. | |
| 6,791,460 B2 | 9/2004 | Dixon et al. | |
| 6,983,499 B2 | 1/2006 | Gladney | |
| 7,089,612 B2 | 8/2006 | Rocher et al. | |
| 7,296,312 B2 | 11/2007 | Menkedick et al. | |
| 7,472,437 B2 | 1/2009 | Riley et al. | |
| 7,676,866 B2 | 3/2010 | Toms et al. | |
| 7,971,295 B2 | 7/2011 | Dippl et al. | |
| 8,039,766 B2 | 10/2011 | Flanagan | |
| 8,258,944 B2 | 9/2012 | Riley et al. | |
| 8,442,738 B2 | 5/2013 | Patmore | |
| 8,502,663 B2 | 8/2013 | Riley et al. | |
| 8,866,610 B2 | 10/2014 | Riley et al. | |
| 8,959,681 B2 | 2/2015 | Richards | |
| 9,009,893 B2 | 4/2015 | Kramer et al. | |
| 9,655,796 B2 * | 5/2017 | Riley | A61G 7/012 |

| | | | |
|---|---|---|---|
| 2001/0032362 A1 | 10/2001 | Welling et al. | |
| 2002/0002742 A1 | 1/2002 | Osborne et al. | |
| 2002/0080037 A1 | 6/2002 | Dixon et al. | |
| 2002/0138906 A1 | 10/2002 | Bartlett et al. | |
| 2004/0177445 A1 | 9/2004 | Osborne et al. | |
| 2004/0231052 A1 | 11/2004 | Gladney | |
| 2005/0035871 A1 | 2/2005 | Dixon et al. | |
| 2005/0166324 A1 | 8/2005 | Dixon et al. | |
| 2005/0172405 A1 | 8/2005 | Menkedick et al. | |
| 2006/0010601 A1 * | 1/2006 | Riley | H01H 3/16 |
| | | | 5/600 |
| 2006/0080777 A1 | 4/2006 | Rocher et al. | |
| 2006/0107459 A1 | 5/2006 | Gladney | |
| 2006/0162079 A1 | 7/2006 | Menkedick et al. | |
| 2006/0168731 A1 | 7/2006 | Menkedick et al. | |
| 2006/0168730 A1 | 8/2006 | Menkedick et al. | |
| 2007/0296600 A1 | 12/2007 | Dixon et al. | |
| 2008/0010748 A1 | 1/2008 | Menkedick et al. | |
| 2009/0064414 A1 * | 3/2009 | Andersen | A61G 1/0275 |
| | | | 5/611 |
| 2012/0317726 A1 | 12/2012 | Riley et al. | |
| 2013/0312183 A1 | 11/2013 | Riley et al. | |
| 2014/0352067 A1 | 12/2014 | Riley et al. | |
| 2016/0038357 A1 | 2/2016 | Riley et al. | |
| 2016/0166453 A1 | 6/2016 | Furman et al. | |
| 2017/0202717 A1 | 7/2017 | Andersen et al. | |

FOREIGN PATENT DOCUMENTS

| | | |
|---|---|---|
| CN | 2624730 | 7/2004 |
| CN | 1539393 A | 10/2004 |
| CN | 204890405 | 12/2015 |
| DE | 3313843 C2 | 1/1986 |
| DE | 3716917 C2 | 7/1996 |
| EP | 1496830 B1 | 1/2005 |
| EP | 1585473 B1 | 8/2009 |
| EP | 2777670 A1 | 2/2016 |
| EP | 3045158 A1 | 4/2018 |
| FR | 2770396 | 5/1999 |
| FR | 2770396 B1 | 3/2000 |
| GB | 2343371 B | 9/2000 |
| JP | 2-156950 | 6/1990 |
| JP | 11299837 A | 11/1999 |
| WO | 9627356 A1 | 9/1996 |
| WO | 9720534 A1 | 6/1997 |
| WO | 0147340 A2 | 7/2001 |
| WO | 2013126461 A1 | 8/2013 |

OTHER PUBLICATIONS

Extended European Search Report for European Patent Application No. 19199901.0 dated Feb. 5, 2020 (7 pages).
European Examination Report dated Feb. 14, 2022.
Second Chinese Office action dated Sep. 27, 2021 with translation.
Third Chinese Office action dated Jan. 17, 2022 with translation.

* cited by examiner

OBSTACLE DETECTION IR BEAM FILTER

PRIORITY CLAIM

This application claims priority to U.S. Provisional Patent Application No. 62/737,504, filed Sep. 27, 2018, which is expressly incorporated by reference herein.

TECHNICAL FIELD

The present application relates to a patient support apparatus including an obstacle detection system. More particularly, the present application relates to an obstacle detection system including an emitter and an infrared beam filter.

BACKGROUND

It is well known to provide a vertically movable patient support. More particularly, it is known to provide a hospital bed including a base frame and an elevating frame supporting a patient support surface. A lifting mechanism is configured to raise and lower the elevating frame relative to the base frame. Entry and exit from the bed is facilitated by placing the elevating frame in a lowered position. A raised position of the elevating frame, in turn, provides a convenient surface for the examination and treatment of a patient supported on the patient support.

SUMMARY

The present application discloses one or more of the features recited in the appended claims and/or the following features which, alone or in any combination, may comprise patentable subject matter.

According to one aspect of the present disclosure, a patient support apparatus includes a first frame having an upper surface, a second frame disposed in spaced-apart parallel relation to the first frame, a lifting device, an emitter, and a receiver. The second frame has a lower surface facing toward the upper surface of the first frame. The second frame is configured to move upward and downward relative to the first frame between a raised position, in which the second frame is spaced apart from the first from by a first distance, and a lowered position, in which the second frame is spaced apart from the first frame by a second distance that is less than the first distance. The lifting device configured to move the second frame relative to the first frame.

In some embodiments, the emitter includes an emitter base coupled to one of the first frame and the second frame, a light source configured to emit a light beam, and an integral beam filter coupled to the emitter base. In some embodiments, the receiver is coupled to one of the first frame and the second frame and arranged to receive the light beam emitted from the emitter. In some embodiments, the lifting device is disabled if an obstacle blocks the light beam emitted by the emitter from being received by the receiver.

In some embodiments, the beam filter is configured to narrow the light beam within a predetermined distance to prevent the light beam from being reflected off the first frame and the second frame and reaching the receiver when the second frame is spaced apart from the first frame by at least the predetermined distance. In some embodiments, the beam filter includes an arm coupled to the emitter base and that extends from the base toward the receiver and a plurality of blinds coupled to a distal end of the arm.

In some embodiments, the emitter base includes a first length and the arm includes a second length and the second length is greater than the first length. In some embodiments, the light emitting diode is spaced apart from the plurality of blinds by the second length.

In some embodiments, the plurality of blinds includes an upper blind arranged generally perpendicular to an upper surface of the arm and the upper blind is spaced apart from the upper surface of the arm. In some embodiments, the plurality of blinds further includes a lower blind spaced apart from the arm and arranged to extend outwardly away from the upper surface of the arm.

In some embodiments, the lower blind includes at least one spacer and a front bumper extending between the left and right spacers and the left and right spacers extend outwardly away from the arm. In some embodiments, the front bumper extends upwardly away from the at least one spacer. In some embodiments, the light emitting diode is spaced apart from the upper blind by a first distance and the light emitting diode is spaced apart from the front bumper of the lower blind by a second distance and the first distance is less than the second distance.

In some embodiments, the plurality of blinds further includes a first peripheral blind and a second peripheral blind, and the upper blind and the peripheral blinds define a window through which the light beam is emitted. In some embodiments, front bumper of the lower blind extends upwardly toward the upper blind and the front bumper is configured to block a portion of the light beam being emitted through the window. In some embodiments, the first and second peripheral blinds extend upwardly from the arm and are generally perpendicular to the upper surface of the arm.

In some embodiments, the arm includes a first width, the window includes a second width that is less than the first width of the arm, and the front bumper of the lower blind includes a third width that is less than the first width of the arm and greater than the second width of the window. In some embodiments, the window is spaced apart from the light emitting diode by a distance equal to about 34 millimeters and the window includes a width equal to about 7.8 millimeters and a height equal to about 4.4 millimeters.

In some embodiments, the emitter base further includes a base locator, and the base locator is configured to properly orient the emitter base relative to the receiver. In some embodiments, the emitter base locator includes a curvilinear flange and a locking tab spaced apart from the curvilinear tab.

In some embodiments, the emitter base further includes an emitter locator, and the emitter locator is configure to properly orient the light source relative to the receiver. In some embodiments, the emitter locator includes a curvilinear flange and a locking tab spaced apart from the curvilinear tab.

In some embodiments, the beam filter is configured to block a portion of the light beam to provide a vertical predetermined range of light having an upper maximum extent and a lower maximum extend that is within the predetermined distance. In some embodiments, the beam filter is configured to block a portion of the light beam to provide a horizontal predetermined range of light having a first lateral maximum extent and a second lateral maximum extend, the first and second lateral maximum extends having a reflection point off the patient support apparatus that is beyond a midway point between the emitter and the receiver.

According to another aspect of the present disclosure, an obstacle detection unit includes an emitter, a receiver, and a beam filter. The emitter includes an emitter base coupled a first frame and configured to emit a light beam. The receiver is coupled to the first frame opposite the emitter and is arranged to receive the light beam from the emitter.

In some embodiments, the integral beam filter is coupled to at least one of the emitter and the receiver. In some embodiments, the beam filter is configured to narrow the light beam within a predetermined distance to prevent the light beam from being reflected off the first frame and a second frame arranged above the first frame and reaching the receiver when the second frame is spaced apart from the first frame by at least the predetermined distance.

In some embodiments, the beam filter includes an arm that extends away from the at least one of the emitter and the receiver and a plurality of blinds coupled to a distal end of the arm. In some embodiments, the plurality of blinds includes an upper blind arranged generally perpendicular to an upper surface of the arm and the upper blind is spaced apart from the upper surface of the arm.

In some embodiments, the plurality of blinds further includes a lower blind spaced apart from the arm and arranged to extend outwardly away from the upper surface of the arm. In some embodiments, the lower blind includes at least one spacer and a front bumper extending between the left and right spacers and the left and right spacers extend outwardly away from the arm. In some embodiments, the front bumper extends upwardly away from the at least one spacer.

In some embodiments, the plurality of blinds further includes a first peripheral blind and a second peripheral blind, and the upper blind and the peripheral blinds define a window through which the light beam is received. In some embodiments, wherein front bumper of the lower blind extends upwardly toward the upper blind and the front bumper is configured to block a portion of the light beam being emitted through the window.

In some embodiments, the first and second peripheral blinds extend upwardly from the arm and are generally perpendicular to the upper surface of the arm. In some embodiments, the arm includes a first width, the window includes a second width that is less than the first width of the arm, and the front bumper of the lower blind includes a third width that is less than the first width of the arm and greater than the second width of the window.

Additional features and advantages of the present invention will become apparent to those skilled in the art upon a consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
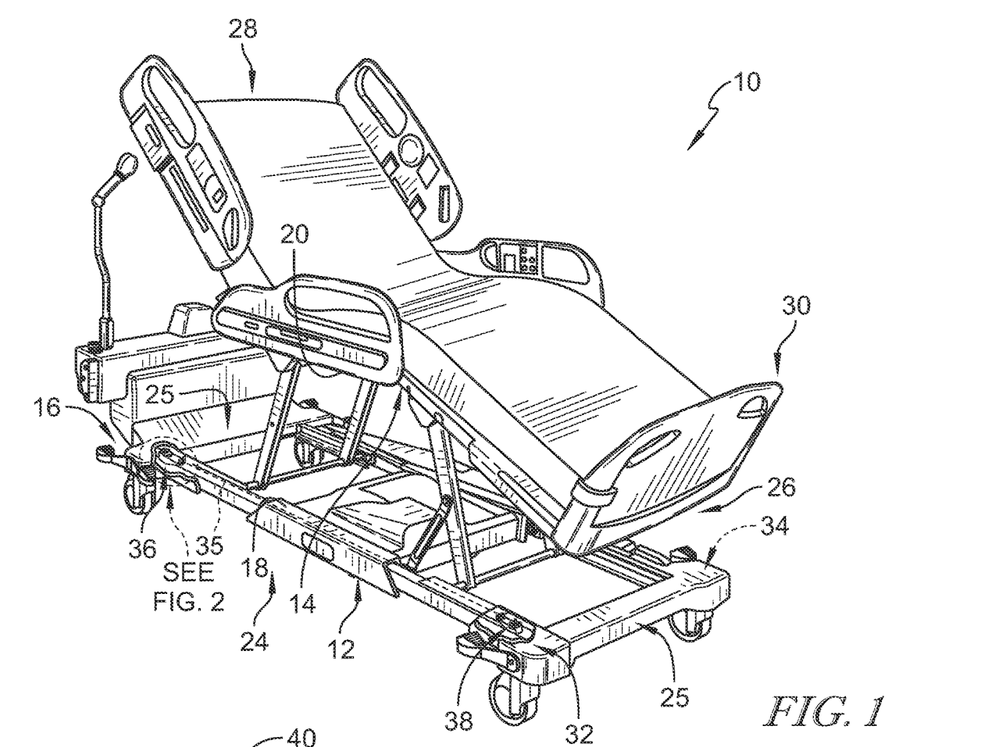
FIG. 1 is a perspective view of a patient-support apparatus including an obstacle detection device, in accordance with the present disclosure.
Figure 2:
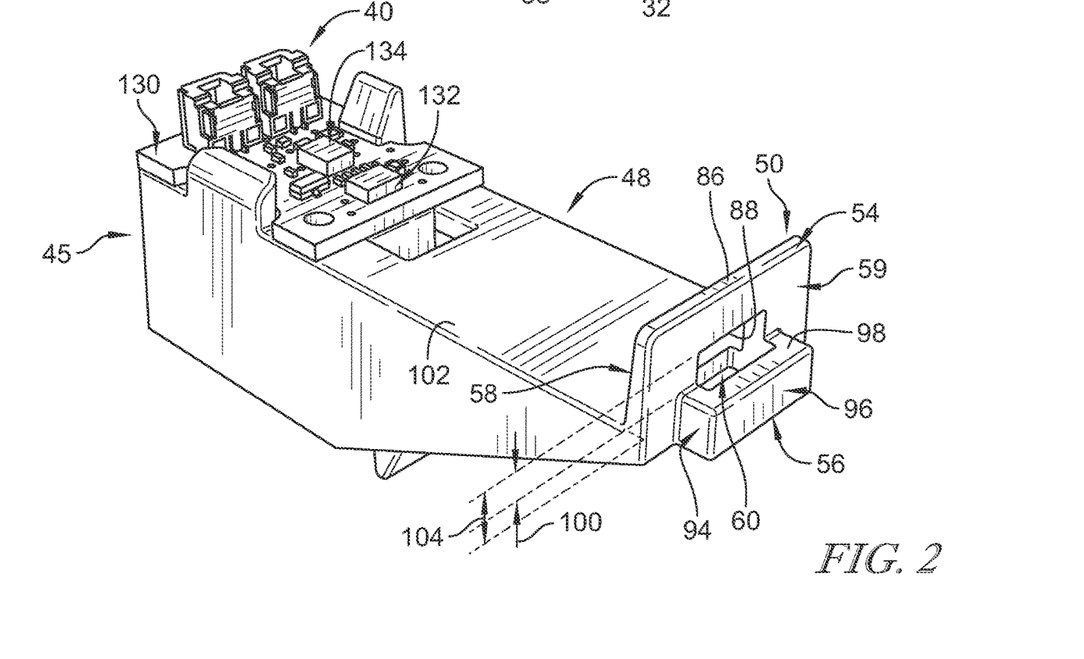
FIG. 2 is a perspective view of an emitter included in the obstacle detection device, the emitter including an integral beam filter coupled to a distal end of an arm.
Figure 3:
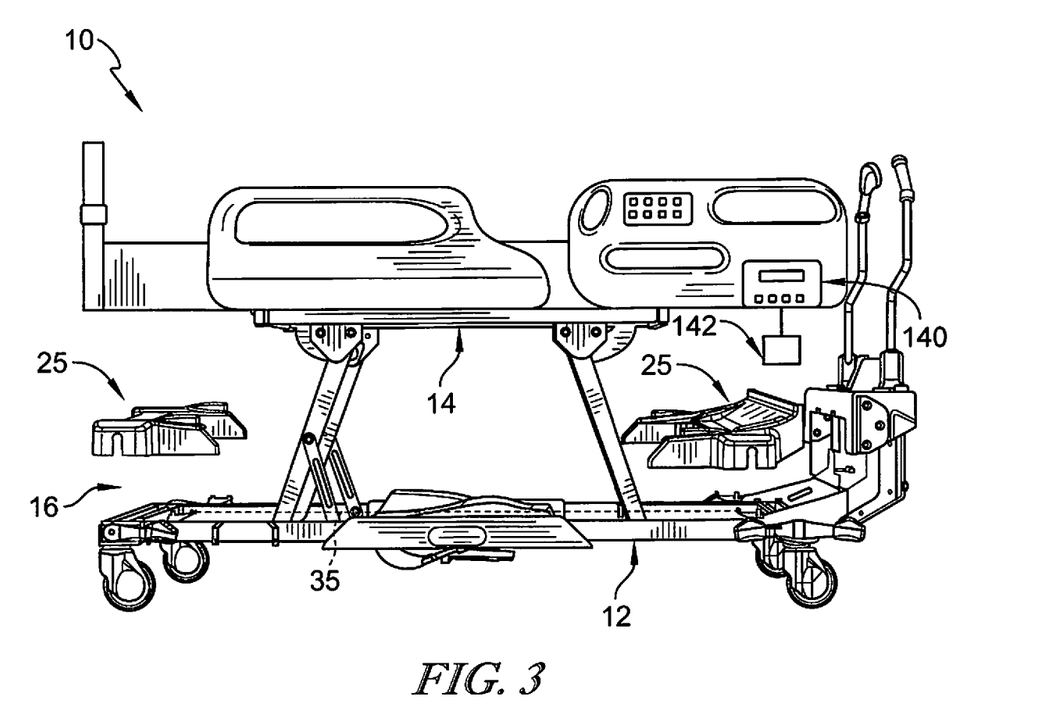
FIG. 3 is a side elevation and partially exploded view of the patient-support apparatus of FIG. 1, illustrating the patient-support apparatus in a fully-raised position and with potential obstacles positioned in detection paths of a receiver.
Figure 4:
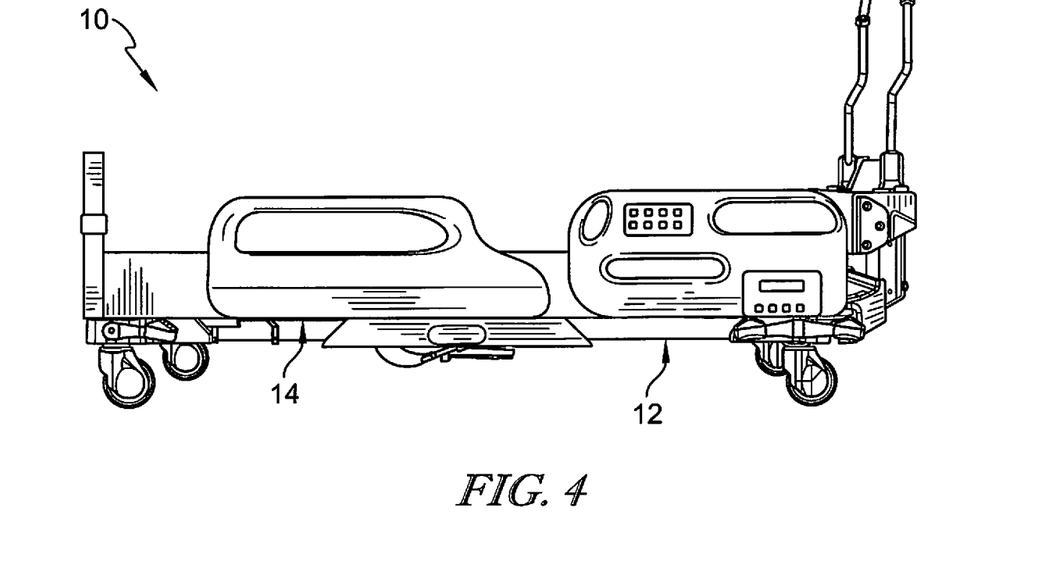
FIG. 4 is a side elevation view similar to FIG. 3, illustrating the patient-support apparatus in a fully-lowered position.

A patient-support apparatus 10 illustratively embodied as a hospital bed, in accordance with the present disclosure, is shown in FIGS. 1-3. An example of a hospital bed is described in U.S. Pat. No. 9,655,796 which is expressly incorporated by reference herein. The patient-support apparatus 10 includes a first or base frame 12 and a second or elevating frame 14. The elevating frame 14 is configured to move vertically between a fully-raised position, as shown in FIG. 3, and a fully-lowered position as shown in FIG. 4. A plurality of intermediate positions are available for the elevating frame 14 between the fully-raised position and the fully-lowered position.

Figure 5:
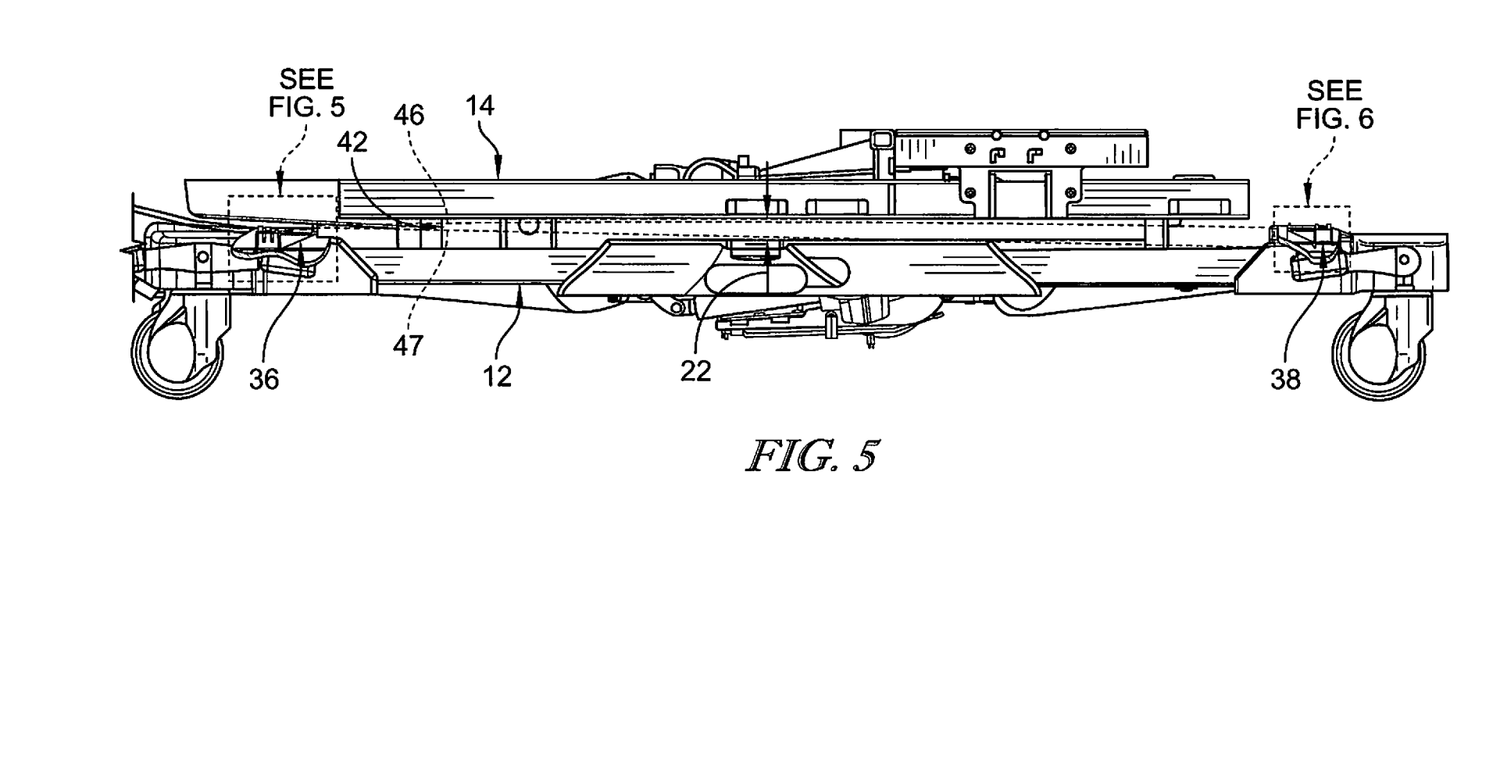
FIG. 5 is an enlarged side elevation view of the obstacle detection device coupled to a first frame of the patient-support apparatus of FIG. 1.
Figure 6:
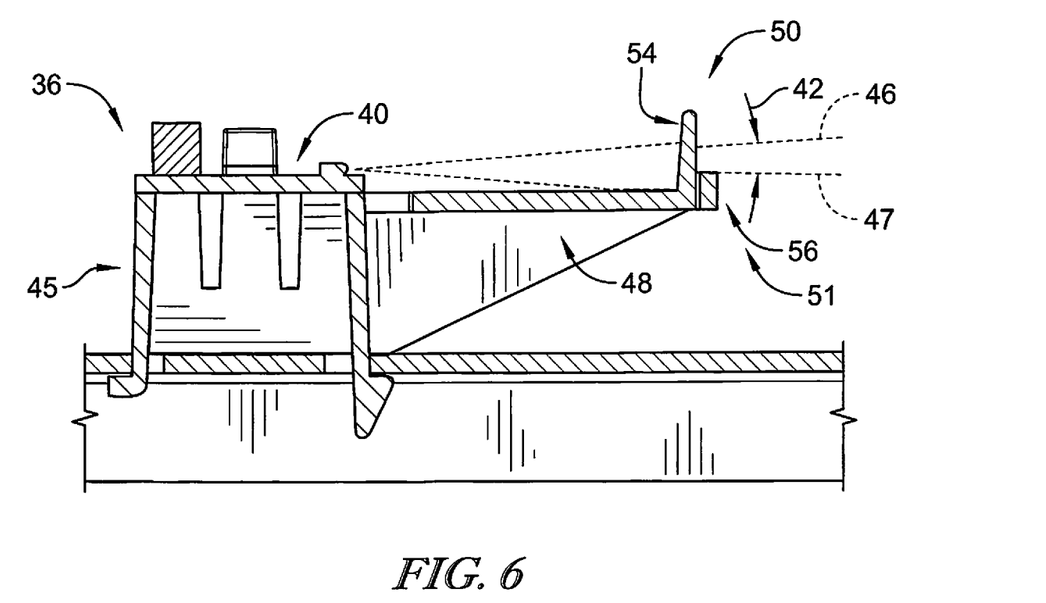
FIG. 6 is a side elevation and sectional view of the emitter and showing that the emitter is configured to emit a beam of light that travels toward the receiver and has a predetermined range in the vertical direction.

The patient-support apparatus 10 further includes an obstacle detection unit 16 coupled to at least one of the base frame 12 or the elevating frame 14 as shown in FIGS. 1 and 2. The obstacle detection unit 16 is configured to detect the presence of one or more obstacles within a predetermined distance 22 between an upper surface 18 of the base frame 12 and a lower surface 20 of the elevating frame 14 as shown in FIG. 5. If an obstacle, such as a human foot, for example, is detected within the predetermined distance 22, the obstacle detection unit 16 is configured to stop or prohibit vertical movement of the elevating frame 14 downward toward the base frame 12. In this way, the obstacle detection unit 16 precludes the obstacle from being damaged or injured by the surfaces 18 and 20.

The patient-support apparatus 10 includes opposing left and right longitudinal side edges 24 and 26 extending between a head end 28 and a foot end 30 as shown in FIGS. 1 and 3. The obstacle detection device 16 includes a first or left side detection unit 32, a second or right side detection unit 34. The first detection unit 32 is positioned along the left side longitudinal edge 24 of the patient-support apparatus 10. The second detection unit 34 is positioned along the right longitudinal side edge 26 of the patient-support apparatus 10. In the illustrative embodiment, each of the detection units 32, 34 are coupled to the base frame 12 of the patient support apparatus 10. However, in other embodiments, the obstacle detection unit 16 may further include additional detection units coupled to the elevating frame 14 of the patient-support apparatus 10.

The left and right detection units 32, 34 are identical to one another in the illustrative embodiment. As such, only the first detection unit 32 is described in detail below. The disclosure related to the first detection unit 32 is expressly incorporated herein for the second detection unit 34. Illustratively, the first detection unit 32 includes an emitter 36 coupled to the base frame 12 and a receiver 38 coupled to the base frame 12 opposite the emitter 36 as shown in FIGS. 1 and 2. The emitter 36 illustratively includes a light source 40, such as an infrared (IR) light emitting diode (LED). The light source 40 forms an infrared light beam 35 that travels toward the receiver 38. The light emitting diode may be empirically selected based upon dimensions and operating conditions of the patient-support apparatus 10. Both the emitter 36 and the receiver 38 are contained within respective enclosures 25.

In the illustrative embodiment, the light source 40 includes a printed circuit board 130, a self-contained infrared (IR) light-emitting diode (LED) 132, and a microprocessor 134 as shown in FIG. 2. The LED 132 and the microprocessor 134 cooperate to generate an infrared signal that is received by the receiver 38. While the illustrative emitters 36 and receivers 38 utilize infrared light, it should be appreciated that other wireless signals may be substituted therefore. More particularly, other forms of electromagnetic radiation, such as ultrasonic, radar, and microwave, may be substituted for IR light.

The emitter 36 further includes an emitter base 45, an arm 48, and a beam filter 50 coupled to a distal end 51 of the arm 48 as shown in FIG. 2. The emitter base 45 supports the light source 40 on the base frame 12. The arm 48 extends away from the emitter base 45 toward the receiver 38 and orients the beam filter 50 relative to the receiver 38. The beam filter 50 is configured to block a portion of the light beam before the light beam is released from the emitter 36 toward the receiver 38.

The beam filter 50 includes an upper blind 54, a lower blind 56, a first or left peripheral blind 58, and a second or right peripheral blind 59 as shown in FIG. 2. The upper blind 54 is coupled to both the first and second peripheral blinds 58, 59 and extends upwardly away from the peripheral blinds 58, 59 and the arm 48. The lower blind 56 is coupled to the distal end of the arm 48 and extends outwardly away from the arm 48. The first and second peripheral blinds 58, are coupled to opposite lateral sides of the arm and extend upwardly away from the arm to locate the upper blind 54 in spaced-apart relation to the arm 48.

The upper blind 54, the lower blind 56, the first peripheral blind 58, and the second peripheral blind 59 cooperate to define a window 60 as shown in FIG. 2. The window 60 permits only a portion of the light beam to pass therethrough. The upper and lower blinds 54 and 56 are configured to block portions of the light beam from exiting the enclosure 25 and reflecting off of various components of the patient-support apparatus 10 and reaching the detector 62 in the vertical direction.

For example, the beam filter 50 narrows the light beam such that any reflection points are beyond a point along the patient-support apparatus 10 where the light beam could be reflected back toward the receiver 38 and provide a false positive reading. Without the beam filter 50, the light beam 35 may reflect off of the patient support apparatus 10, proceed around an obstacle located between the base frame 12 and the elevating frame 14 and still reach the receiver 38. As such, the elevating frame 14 may still be permitted to move toward the fully-lowered position, thereby harming the obstacle along the way. The beam filter 50 is provided on the emitter 36, and a corresponding beam filter 66 is provided on receiver 38, to prevent this type of situation.

The upper blind 54 includes an upper end 86 and a lower end 88. The upper end 86 extends upwardly from away from the arm 48 as shown in FIGS. 2 and 5. The lower end 88 defines an upper surface of the window 60. The lower blind 56 includes a plurality of spacers 94 and a front bumper 96 coupled to the spacers 94. The spacers 94 extend outwardly from the distal end of the arm 48. The front bumper 96 extends upwardly from the spacers 94 and blocks a portion of the light beam before the light beam is sent to the receiver 38. The front bumper 96 has an upper surface 98 that is spaced apart from the lower end 88 of the upper blind 54 a distance 100 while an upper surface 102 of the arm is spaced apart from the lower end 88 a distance 104 that is greater than the distance 100. In the illustrative embodiment, the distance 100 is equal to about 2.6 millimeters while the distance 104 is equal to about 4.4 millimeters.

In the illustrative embodiment, the light beam spreads outward at an angle of about 4.5 degrees from the light source 40 as the light beam extends away from the light source 40 as shown in FIG. 5. The beam filter 50 is sized and located to narrow the light beam range to a predetermined range 42 that has an upper maximum extent 46 and a lower maximum extent 47. The upper blind 54 is sized and located to provide the upper maximum extent 46 of the predetermined range 42. The lower blind 56 is sized and located to provide the lower maximum extent 47 of the predetermined range 42. The first and second peripheral blinds 58 and 59 are sized and located to provide lateral maximum extents 82, 84 of a horizontal predetermined range 80, as will be described in greater detail below.

The vertical predetermined range 42 is within the predetermined distance 22 in the illustrative embodiment. The emitter 36 and the receiver 38 cooperate to eliminate reflection of the light source 40 off of the base frame 12 and the elevating frame 14 and reaching the receiver 38. As such, the emitter 36 and the receiver 38 cooperate to block a portion of the light source 40 from reaching the receiver 38 while an obstacle is located within the predetermined range 22 and, therefore, prevent false positives from being detected by the receiver 38.

The emitter base 45 has a first length and the arm 48 has a second length that is greater than the first length. The beam filter 50 is coupled to the distal end of the arm 48 and is spaced apart from the light source 40 by the second distance so that the beam filter 50 blocks a portion of the light beam. In the illustrative embodiment, the second distance is equal to about 34 millimeters.

Figure 7:
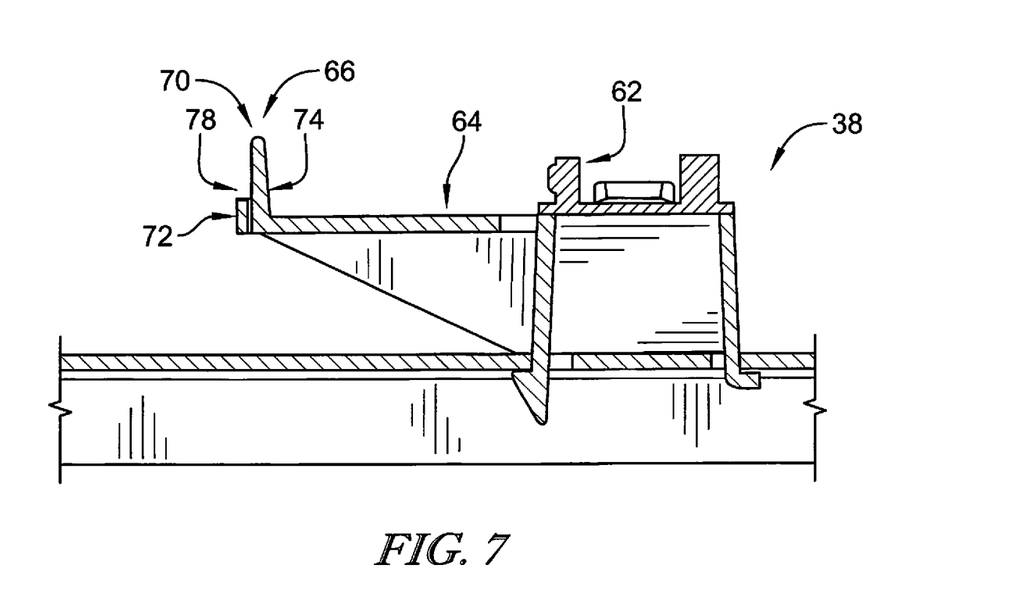
FIG. 7 is a side elevation view of the receiver included in the obstacle detection device of FIG. 5.

The receiver 38 illustratively includes a detector 62, an arm 64, and a beam filter 66 coupled to a distal end 68 of the arm 64 as shown in FIG. 7. The detector 62 is configured to detect the light beam emitted from the window 60 of the emitter 36 in the absence of an obstacle within the predetermined distance 22. In the illustrative embodiment, the arm 64 and the beam filter 66 of the receiver 38 are identical to the arm 48 and the beam filter 50 of the emitter 36. The arm 64 and the beam filter 66 are sized and located relative to the detector 62 to block the light beam from reflecting off of various components of the patient-support apparatus 10 and reaching the detector 62.

The beam filter 66 of the receiver 38 includes an upper blind 70, a lower blind 72, a first or left peripheral blind 74, and a second or right peripheral blind 76 as shown in FIG. 7. The upper blind 70, the lower blind 72, the first peripheral blind 74, and the second peripheral blind 76 cooperate to define a window 78. The window 78 is spaced apart from the detector 62 and is configured to admit only a portion of the light beam that travels within the predetermined distance 22 to the receiver 38. As such, the window 78 helps guide the light beam within the predetermined range 42 toward the detector 62.

Figure 8:
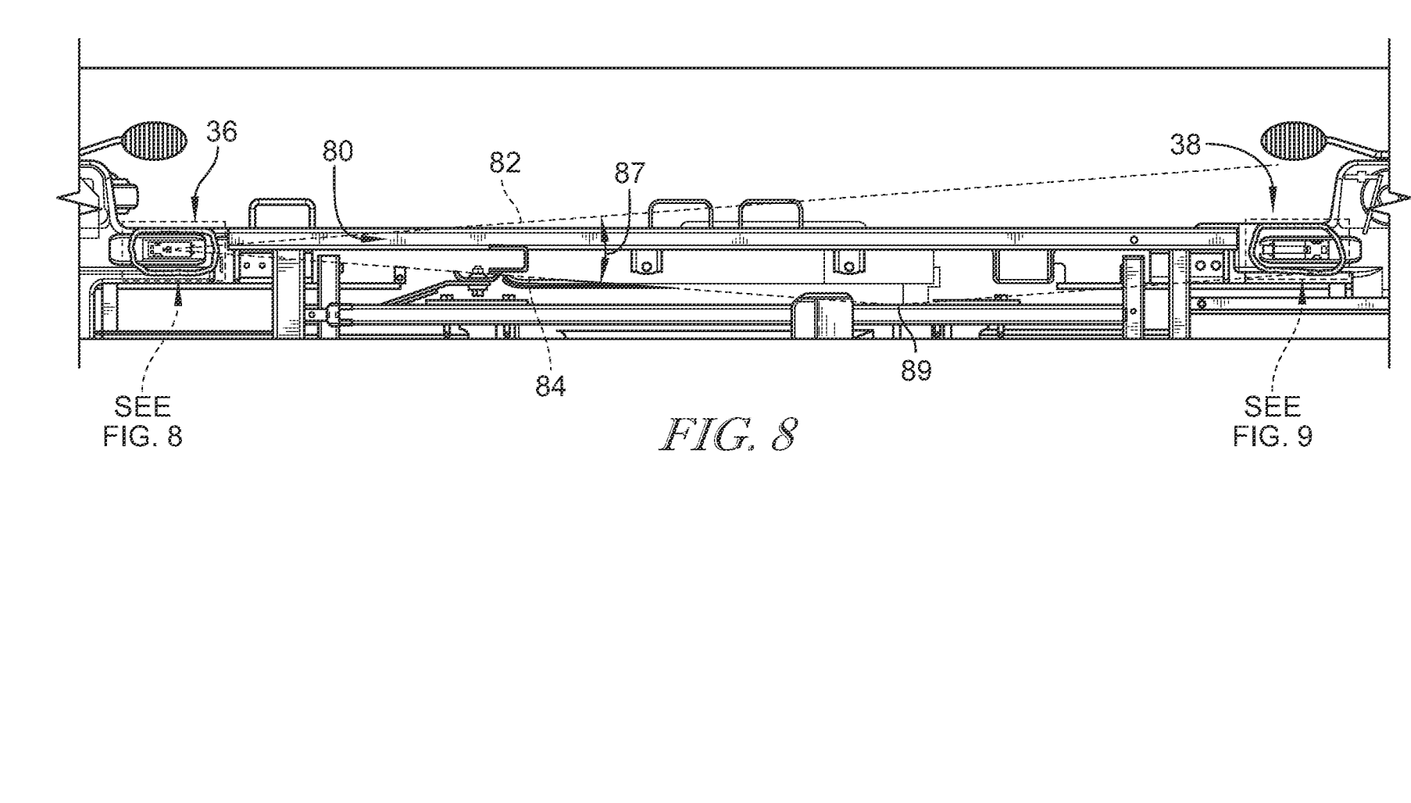
FIG. 8 is a top view of the obstacle detection device of FIG. 1 and showing that the beam of light has a predetermined range in the horizontal direction as the beam travels toward the receiver.

Turning now to FIG. 8, the first and second peripheral blinds 58 and 59 of the emitter 36 are configured to narrow the light beam to a horizontal predetermined range 80. The predetermined range 80 includes a first or left maximum extent 82 and a second or right maximum extent 84. The first and second peripheral blinds 58 and 59 are sized and located to provide the first and second maximum extents 82 and 84 of the horizontal predetermined range 80. In one example, the first and second lateral maximum extents 82, 84 have at least one reflection point 89 off the patient support apparatus that is beyond a midway point between the emitter 36 and the receiver 38.

Figure 9:
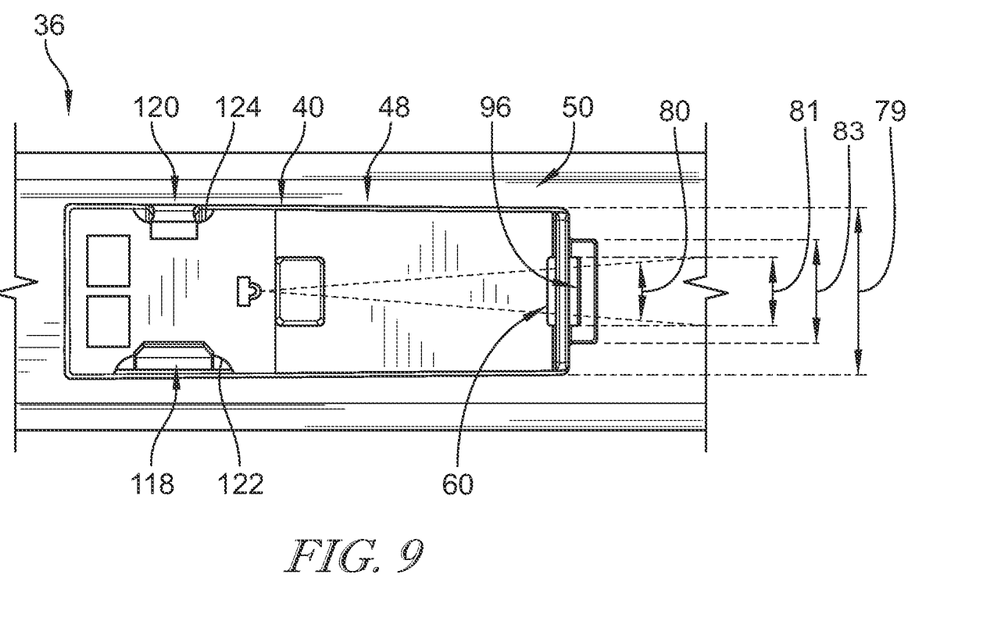
FIG. 9 is a top view of the emitter of FIG. 8.

The first and second peripheral blinds 58 and 59 are configured to block the light beam from reflecting off of various components of the patient-support apparatus 10 and reaching the detector 62 in the horizontal direction as suggested in FIGS. 8 and 9. For example, the peripheral blinds 58 and 59 are sized and located such that the light beam emanates from the window 60 at an angle r that corresponds with a reflection point 89 off the patient-support apparatus 10. The reflection point 89 is beyond any point along the patient-support apparatus 10 where the light beam could be reflected back toward the receiver 38 and provide a false positive reading.

Figure 10:
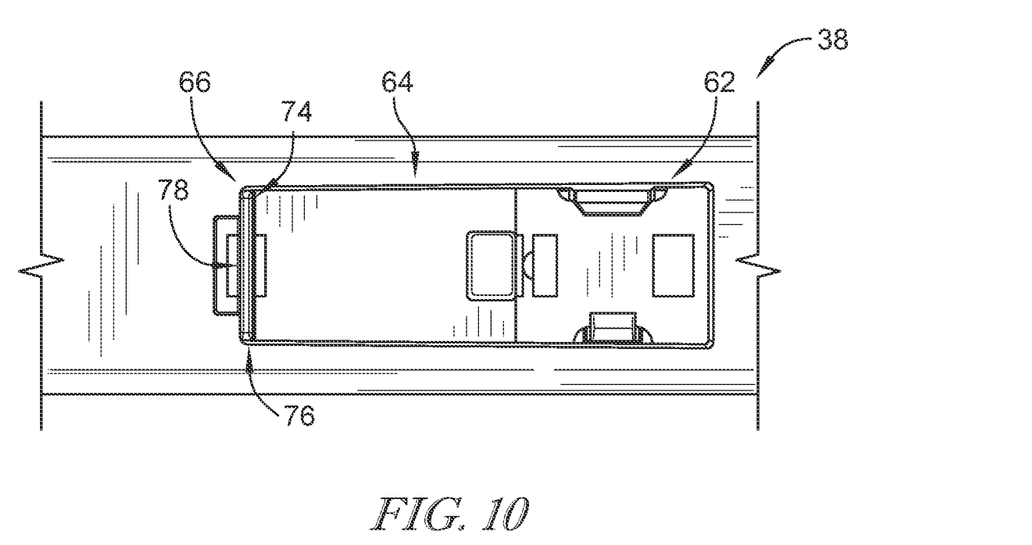
FIG. 10 is a top view of the receiver of FIG. 8.

In the illustrative embodiment, the arm 48 includes a first width 79 and the window 60 includes a second width 81 that is less than the first width 79 of the arm 48. The front bumper 96 of the lower blind 56 includes a third width 83 that is less than the first width 79 of the arm 48 and greater than the second width 81 of the window 60. The window 78 is identical to window 60 and is spaced apart from the detector 62 to help guide the light beam within the predetermined range 80 toward the detector 62 as suggested in FIG. 10. In the illustrative embodiment, each window 60, 78 has a width equal to about 7.8 millimeters.

Figure 11:
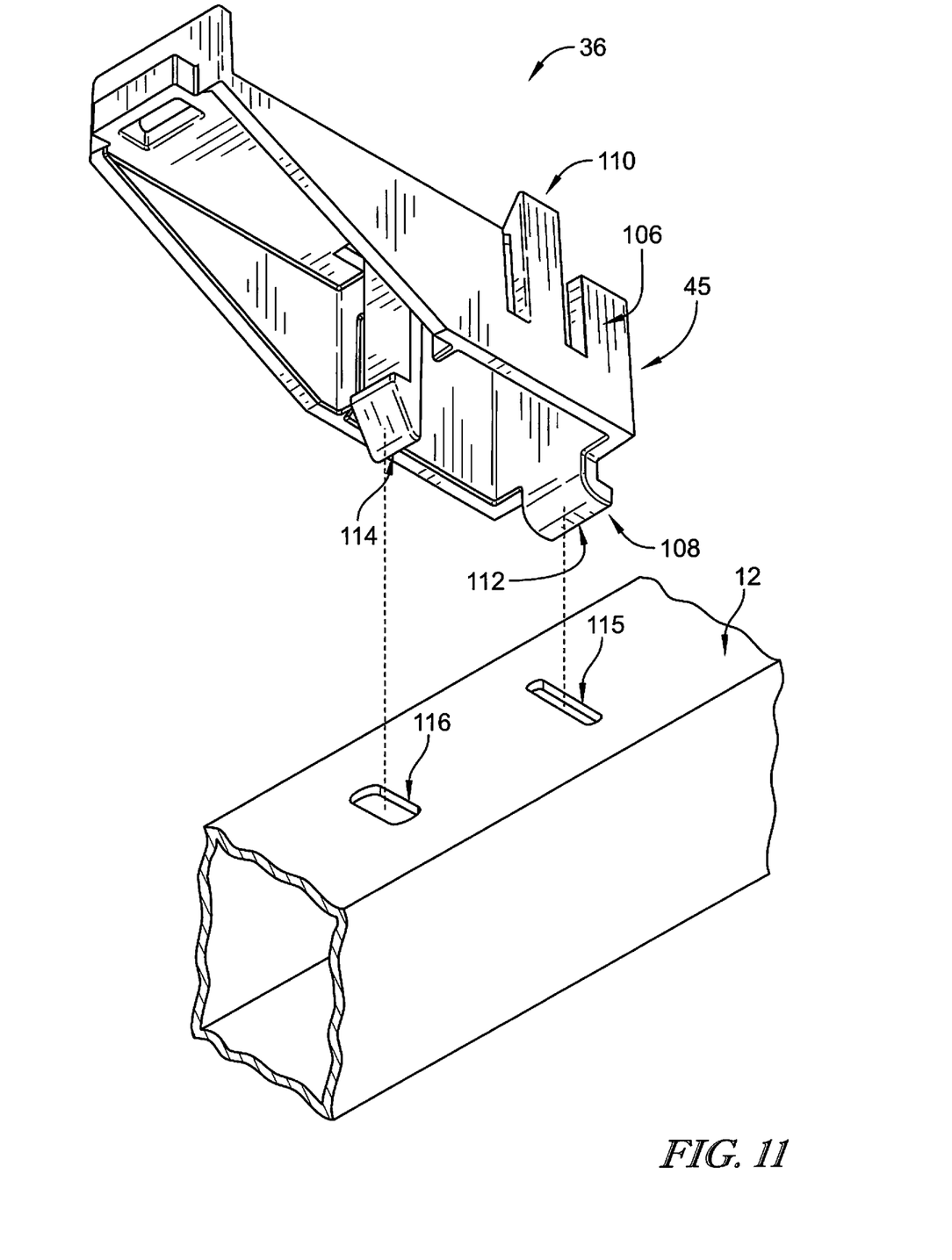
FIG. 11 is another perspective view of the emitter of FIG. 2 showing that the emitter further includes a location feature that is configured to properly orient the emitter on the base frame.

Turning now to FIG. 11, the emitter base 45 includes a pedestal 106 an emitter mount 108, and a light source mount 110. The pedestal 106 supports the light source 40 on the base frame 12 of the occupant-support apparatus 10. The emitter mount 108 couples the emitter 36 to the base frame 12 of the occupant-support apparatus 10. The light source mount 110 couples and retains the light source 40 to the emitter base 45.

The emitter mount 108 includes a curvilinear flange 112 and a locking tab 114 as shown in FIG. 11. During assembly, the curvilinear flange is first positioned in a corresponding flange aperture 115 formed in the base frame 12. The emitter 36 is then pivoted downward until the locking tab is positioned in a corresponding tab aperture 116 formed in the base frame 12. The flange 112 and the tab 114 are sized according to their respective apertures 115, 116. In this way, the curvilinear flange 112 and the locking tab 114 cooperate to properly orient the emitter 36 on the base frame 12.

The light source mount 110 includes a curvilinear flange 118 and a locking tab 120 that extend upwardly from the pedestal 106 as shown in FIGS. 9 and 11. The curvilinear flange 118 corresponds to a cutout 122 formed in the light source 40. The locking tab 120 corresponds to a cutout 124 formed in the light source 40 that is opposite the cutout 122. During assembly, the cutout 122 is aligned with the curvilinear flange 118. The light source 40 is then pivoted downward until the cutout 124 is aligned with the locking tab 120. In this way, the curvilinear flange 118 and the locking tab 120 cooperate with respective cutouts 122, 124 to properly orient the light source 40 on the pedestal 106.

The receiver 38 includes identical mounts to those described above regarding emitter mount 108 and light source mount 110. The mounts included in the receiver 38 are configured to properly orient the receiver 38 relative to the base frame 12 and the detector 62 relative to the light source 40. As such, the disclosure relating to the mounts 108, 110 is incorporated by reference to receiver 38.

In illustrative embodiments, the patient-support apparatus 10 may further include a controller that is configured to regulate vertical movement of the elevating frame 14 relative to the base frame 12. A non-limiting example of such a controller is described in U.S. Pat. No. 9,655,796, which is expressly incorporated by reference herein. During operation, the elevating frame 14 may be spaced apart from the base frame 12 in the fully-raised position. A caregiver may wish to lower the elevating frame 14 downward toward the base frame 12 to the fully-lowered position. The controller is configured to determine if an obstacle is located in within the predetermined distance 22 and stop downward movement of the elevating frame if an obstacle is present.

If an obstacle is determined to be present, the controller may also output a command signal to cause an alert or a notification. In some embodiments, the alert or notification may be an audible alarm produced by a loudspeaker 142 or another suitable sound-producing device such as a piezoelectric buzzer, for example. In some embodiments, the audible alarm includes a plurality of pulsed beeps that may be emitted from the loudspeaker 142. In another embodiment, an audible message may be emitted from the loudspeaker 142. The audible message may indicate the side of the patient support apparatus 10 where the obstacle was detected. For example, a pre-programmed message may be emitted from the loudspeaker stating: "obstacle is detected on the left" or "obstacle is detected on the right," as the case may be.

In other embodiments, the alert or notification may be in the form of a pop-up window having a text message that is displayed on a user interface 140. The text message may be the same as the audible message mentioned previously. In some embodiments the user interface 140 is in the form of a touchscreen. In other embodiments the user interface may include a plurality of associated buttons configured to receive inputs from a user or caregiver. Embodiments in which a text message is provided on user interface 140 and in which an audible message is sounded by loudspeaker 142 are also contemplated.

In illustrative embodiments, the right and left side detection units 32, 34 may have their emitters 36 positioned at the head end 28 and foot end 30 of the patient-support apparatus 10. As such, the transmission of infrared light from the emitters 36 of the right side detection unit 32 and the left side detection unit 34 will be in opposite directions in order to reduce the possibility of cross talk between the two detection units 32, 34.

Although the invention has been described in detail with reference to certain illustrated embodiments, variations and modifications exist within the scope and spirit of the invention as described and as defined in the following claims.

The invention claimed is:

1. A patient support apparatus comprising
a first frame having an upper surface,
a second frame disposed in spaced-apart parallel relation to the first frame, the second frame having a lower surface facing toward the upper surface of the first frame, the second frame configured to move upward and downward relative to the first frame between a raised position, in which the second frame is spaced apart from the first from by a first distance, and a lowered position, in which the second frame is spaced apart from the first frame by a second distance that is less than the first distance, a lifting device configured to move the second frame relative to the first frame, an emitter including an emitter base coupled to one of the first frame and the second frame, a light source configured to emit a light beam, and an integral beam filter coupled to the emitter base, and a receiver coupled to one of the first frame and the second frame and arranged to receive the light beam emitted from the emitter, wherein the lifting device is disabled if an obstacle blocks the light beam emitted by the emitter from being received by the receiver, wherein the beam filter is configured to narrow the light beam within a predetermined distance to prevent the light beam from being reflected off the first frame and the second frame and reaching the receiver when the second frame is spaced apart from the first frame by at least the predetermined distance, and wherein the beam filter includes an arm coupled to the emitter base and that extends from the base toward the receiver and a plurality of blinds coupled to a distal end of the arm.

2. The patient support apparatus of claim 1, wherein the emitter base includes a first length and the arm includes a second length and the second length is greater than the first length.

3. The patient support apparatus of claim 2, wherein the light emitting diode is spaced apart from the plurality of blinds by the second length.

4. The patient support apparatus of claim 1, wherein the plurality of blinds includes an upper blind arranged generally perpendicular to an upper surface of the arm and the upper blind is spaced apart from the upper surface of the arm.

5. The patient support apparatus of claim 4, wherein the plurality of blinds further includes a lower blind spaced apart from the arm and arranged to extend outwardly away from the upper surface of the arm.

6. The patient support apparatus of claim 5, wherein the lower blind includes at least one spacer and a front bumper extending between the left and right spacers and the left and right spacers extend outwardly away from the arm.

7. The patient support apparatus of claim 6, wherein the front bumper extends upwardly away from the at least one spacer.

8. The patient support apparatus of claim 6, wherein the light emitting diode is spaced apart from the upper blind by a first distance and the light emitting diode is spaced apart from the front bumper of the lower blind by a second distance and the first distance is less than the second distance.

9. The patient support apparatus of claim 5, wherein the plurality of blinds further includes a first peripheral blind and a second peripheral blind, and the upper blind and the peripheral blinds define a window through which the light beam is emitted.

10. The patient support apparatus of claim 1, wherein the emitter base further includes a base locator, and the base locator is configured to properly orient the emitter base relative to the receiver.

11. The patient support apparatus of claim 1, wherein the emitter base further includes an emitter locator, and the emitter locator is configure to properly orient the light source relative to the receiver.

12. The patient support apparatus of claim 1, wherein the beam filter is configured to block a portion of the light beam to provide a vertical predetermined range of light having an upper maximum extent and a lower maximum extent that is within the predetermined distance.

13. The patient support apparatus of claim 1, wherein the beam filter is configured to block a portion of the light beam to provide a horizontal predetermined range of light having a first lateral maximum extent and a second lateral maximum extent, the first and second lateral maximum extents having a reflection point off the patient support apparatus that is beyond a midway point between the emitter and the receiver.

14. An obstacle detection unit comprising
an emitter including an emitter base coupled to a first frame and configured to emit a light beam,
a receiver coupled to the first frame opposite the emitter and arranged to receive the light beam from the emitter, and
an integral beam filter coupled to at least one of the emitter and the receiver,
wherein the beam filter is configured to narrow the light beam within a predetermined distance to prevent the light beam from being reflected off the first frame and a second frame arranged above the first frame and reaching the receiver when the second frame is spaced apart from the first frame by at least the predetermined distance, and
wherein the beam filter includes an arm that extends away from the at least one of the emitter and the receiver and a plurality of blinds coupled to a distal end of the arm.

15. The obstacle detection unit of claim 14, wherein the plurality of blinds includes an upper blind arranged generally perpendicular to an upper surface of the arm and the upper blind is spaced apart from the upper surface of the arm.

16. The obstacle detection unit of claim 14, wherein the plurality of blinds further includes a lower blind spaced apart from the arm and arranged to extend upwardly away from the upper surface of the arm.

17. The obstacle detection unit of claim 14, wherein the plurality of blinds further includes a first peripheral blind and a second peripheral blind, and the upper blind and the peripheral blinds define a window through which the light beam is received.

18. The obstacle detection unit of claim 14, wherein the arm includes a first width, the window includes a second width that is less than the first width of the arm, and the front bumper of the lower blind includes a third width that is less than the first width of the arm and greater than the second width of the window.

* * * * *

UNITED STATES PATENT AND TRADEMARK OFFICE
CERTIFICATE OF CORRECTION

| | | |
|---|---|---|
| PATENT NO. | : 11,406,548 B2 | Page 1 of 1 |
| APPLICATION NO. | : 16/559731 | |
| DATED | : August 9, 2022 | |
| INVENTOR(S) | : Michael Buccieri et al. | |

It is certified that error appears in the above-identified patent and that said Letters Patent is hereby corrected as shown below:

In the Claims

In Claim 11, Column 10, Line 7, delete "configure" and insert in its place --configured--.

Signed and Sealed this
Fourth Day of October, 2022

Katherine Kelly Vidal
Director of the United States Patent and Trademark Office